United States Patent
Maier

(10) Patent No.: US 6,872,690 B2
(45) Date of Patent: Mar. 29, 2005

(54) HERBICIDAL 2-ALKYNYL-PYRI (MI) DINES

(75) Inventor: Thomas Maier, Stockach (DE)

(73) Assignee: WYETH, Madison, NJ (US)

( * ) Notice: Subject to any disclaimer, the term of this patent is extended or adjusted under 35 U.S.C. 154(b) by 0 days.

(21) Appl. No.: 10/087,066

(22) Filed: Mar. 1, 2002

(65) Prior Publication Data
US 2003/0073581 A1 Apr. 17, 2003

Related U.S. Application Data

(60) Provisional application No. 60/274,755, filed on Mar. 9, 2001.

(51) Int. Cl.$^7$ .................... C07D 401/12; A01N 43/56
(52) U.S. Cl. .................... 504/250; 504/251; 504/252; 504/253; 504/254; 504/255; 504/256; 504/257; 504/258; 546/261; 546/276.1; 546/280.4; 546/281.4; 546/290; 546/297; 546/298; 546/300; 546/301; 546/302
(58) Field of Search .................... 546/261, 276.1, 546/280.4, 281.4, 290, 297, 298, 299, 300, 301, 302; 504/250, 251, 252, 253, 254, 255, 256, 257, 258

(56) References Cited

U.S. PATENT DOCUMENTS

| | | | |
|---|---|---|---|
| 4,814,403 A | 3/1989 | Dussart-Lermusiaux et al. | 526/265 |
| 5,750,705 A | 5/1998 | Hamprecht et al. | 546/297 |
| 5,849,920 A | 12/1998 | Hamprecht et al. | 546/268 |

FOREIGN PATENT DOCUMENTS

| | | | |
|---|---|---|---|
| DE | 4029654 | 4/1992 | ......... C07D/239/52 |
| EP | 0 318 083 | 5/1989 | |
| FR | 2605010 | 4/1988 | ........... C08G/65/48 |
| JP | 59-152303 | * 8/1984 | |
| JP | 59-157004 | * 9/1984 | |
| WO | WO 92/08714 | * 5/1992 | |
| WO | WO 98/21199 | 5/1998 | |
| WO | WO 99/55693 | 11/1999 | |
| WO | WO 0046184 | * 8/2000 | |

OTHER PUBLICATIONS

Sekiguchi et al., Chem. Abstract 115:256727, 1991.*
Ziessel et al., Chem. Abstract 134:193375, 2000.*
Romero et al., Chem. Abstract 130:296640, 1999.*
Nakayama et al., Chem. Abstract 129:189329, 1998.*
Nitschke et al., Chem. Abstract 128:321535, 1998.*
Chamchoumis et al., Chem. Abstract 131:82037, 1999.*
Houghton et al., Chem. Abstract 127:256664, 1997.*
Ziessel et al., Chem. Abstract 125:221516, 1996.*
Inouye et al., Chem. Abstract 124:146602, 1995.*
Koevari et al., Chem. Abstract 123:198925, 1995.*
Potts et al., Chem. Abstract 118:233840, 1993.*
Butler et al., Chem. Abstract 115:207819, 1991.*
Comprehensive Organic Synthesis, vol. 7, pp. 748–750, B.M. Trost, Ed., Pergamon Press, NY.
Advances in Heterocyclic Chemistry, vol. 9, pp. 285–291, A.R. Katritzky, Ed., Academic Press, NY (1968).
Advances in Heterocyclic Chemistry, vol. 22, pp. 390–392, A.R. Katritzky, Ed., Academic Press, NY (1978).
Advances in Heterocyclic Chemistry, vol. 43, pp. 149–161, A.R. Katritzky, Ed., Academic Press, NY (1988).
D.E. Rudisill et al., J. Org. Chem; 54; (1989), pp. 5856–5866.
Castro et al., J. Org. Chem., 28; (1963) p. 2163.
Stephens et al., J. Org. Chem., 28 (1963) p. 3313–3315.

* cited by examiner

Primary Examiner—Deepak Rao
(74) Attorney, Agent, or Firm—Keil & Weinkauf

(57) ABSTRACT

The invention relates method of combating undesired plant growth at a locus, comprising application to the locus of an effective amount of at least one compound of formula (I):

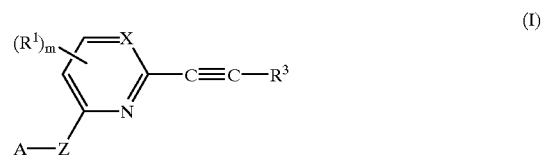

wherein $R^1$, $R^3$, A, X, Z and m have the meaning given in claim 1, and the agronomically acceptable salts or N-oxides thereof, and to novel compounds of formula I as well as to herbicidal compositions containing such compounds as active ingredients.

20 Claims, No Drawings

HERBICIDAL 2-ALKYNYL-PYRI(MI)DINES

This application claims the benefit under 35 USC 119(e) of provisional application 60/274,755, filed Mar. 9, 2001.

BACKGROUND OF THE INVENTION

This invention relates to method of combating undesired plant growth using certain 2-alkynyl-pyri(mi)dines, to novel 2-alkynyl-pyri(mi)dines, to the preparation of these compounds, and to herbicidal compositions containing such compounds.

Pyridines, pyrimidines and their derivatives have many uses in the pharmaceutical area as well as in agriculture (herbicides, fungicides, acaricides, anthelmintics, bird repellents), as reagents, intermediates and chemicals for the polymer and textile industry.

The German patent application DE 40 29 654 discloses fungicidal 2-phenyl-4-alkynyloxy-pyrimidines. However, there is no hint to 2-alkynyl-pyrimidines nor any motivation that such compounds could show herbicidal activity.

The French patent application FR 2 605 010 describes polymers obtainable by thermal polymerization of bis-(2-ethynyl-pyrid-6-yloxy)-arenes. There is no hint that those oligomers could exhibit any herbicidal activity at all.

The compounds according to the present invention combine high herbicidal activity with good selectivity and a desirable rate of degradation in soil.

SUMMARY OF THE INVENTION

The present invention provides a method of combating undesired plant growth with the aid of the compounds of formula I

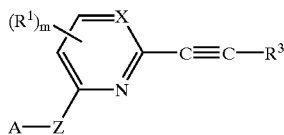

(I)

wherein

X represents N or $CR^2$;

$R_1$ each independently represent a halogen atom or an optionally substituted alkyl, alkenyl, alkinyl, alkoxy, alkoxyalkyl, alkoxy-alkoxy, group or a haloalkyl, haloalkoxy, cyano, nitro or $SF_5$ group; or a —$S(O)_p$—$R^4$ group, in which p is 0, 1 or 2, and $R^4$ represents an alkyl or haloalkyl group; or —$NR^5R^6$, in which $R^5$ and $R^6$ each independently represent a hydrogen atom, an alkyl, alkenyl, aralkyl or aryl group, or $R^7O$—CY—, in which $R^7$ represents an alkyl group, and Y represents O or S;

$R^2$ represents a hydrogen atom or has the meaning given for $R^1$;

$R^3$ represents a hydrogen atom or a formyl group or an optionally substituted alkyl, alkenyl, trialkylsilyl or phenyl group, or an optionally substituted 5- or 6-membered nitrogen-containing heteroaromatic group;

A represents an optionally substituted phenyl group, an optionally substituted 5- or 6- membered nitrogen-containing heteroaromatic group or an optionally substituted thienyl group;

Z represents an oxygen or sulfur atom or a single bond;

m is 0, 1 or 2;

and the agronomically acceptable salts or N-oxides thereof.

The compounds show an excellent selective herbicidal activity in certain crops, such as maize and rice, and degrade well in soil.

It is an object of the present invention to provide the novel herbicidal compounds of formula I, provided that bis-(2-ethynyl-pyrid-6-yloxy)-1,3-benzene, bis-[2-(2-trimethylsilylethynyl) -pyrid-6-yloxy]-1,3-benzene, bis-[2-(3,3-dimethyl-3-hydroxy-prop-1-ynyl)-pyrid-6-yloxy]-1,3-benzene, bis-((2-ethynyl-pyrid-6-yloxy)-4-phenyl)-2,2-propane, bis-((2-ethynyl-pyrid-6-yloxy)-4-phenyl)-2,2-1,1,1,3,3,3-hexafluoropropane, and bis-((2-ethynyl-pyrid-6-yloxy)-4-phenyl)-sulfur are excluded.

It is another object of the invention to provide selective herbicidal compositions containing the new compounds as active ingredients.

It is another object of the invention to provide new processes for the preparation of the new compounds.

These and other objects and features of the invention will become ore apparent from the detailed description set forth hereinbelow.

DETAILED DESCRIPTION OF THE PREFERRED EMBODIMENTS

It has surprisingly been found that the compounds of formula I, in which $R^1$ through $R^3$, A, X, Z and m have the meaning given above, show excellent herbicidal activity against a broad range of weeds.

The expression "pyri(mi)dine" as used hereinbefore or hereinbelow includes both pyridine and pyrimidine moieties. The expression "azolyl" as used hereinbefore or hereinbelow includes 5-membered heteroaryl groups containing at least one nitrogen atom.

An aryl group as substituent or part of other substituents or in the definition of A is suitably an optionally substituted phenyl group. Within the definition of A the 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, thienyl, pyridyl, pyrazinyl, pyrimidyl, pyridazinyl, isoxazolyl, isothiazolyl and triazinyl groups. As far as A is concerned, the definition "aryl" also includes bicyclic systems which consist of a benzene ring fused with a 5- or 6-membered heterocyclic ring as defined above and in turn the 5- or 6-membered heterocycles may be fused with a benzene ring.

One preferred embodiment of the invention is a compound in which A is a difluorobenzodioxolyl group of formula

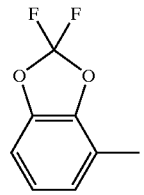

A especially preferred represents a phenyl, pyridyl, thienyl or pyrazolyl group being substituted by one or more of the same or different substituents selected from halogen atoms, alkyl groups, alkoxy groups, cyano groups, haloalkyl groups, haloalkoxy groups, alkylthio groups, haloalkylthio groups and $SF_5$ groups, and preferably has a substituent in the meta-position relative to the point of attachment; more preferably A is meta-substituted by a fluorine or chlorine atom, or a trifluoromethyl, trifluoromethoxy or difluoromethoxy group. If A represents a thienyl group, it may be attached in the 2- or 3-position with respect to the sulfur atom. 3-thienyl groups are preferred.

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably mono-, di-, tri- or perfluoroalkyl, -alkoxy and -alkylthio, especially trifluoromethyl, pentafluoroethyl, trifluoromethoxy, difluoromethoxy, difluoromethylthio, trifluoromethylthio or 2,2,2-trifluoroethoxy groups.

When any groups are designated as being optionally substituted, the optional substituent groups may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxy, phenoxy, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkyl-thio, $C_{1-4}$-alkylsulfonyl and halosulfanyl groups such as $SF_5$. In the case of phenyl-groups 1 to 5 substituents may suitably be employed, in the case of thienyl-groups 1 to 3 substituents may suitably be employed, 1 or 2 substituents being preferred.

Synthetic methods for the preparation of N-oxides of heterocycles are very well known by one skilled in the art including the oxidation of heterocycles with peroxy acids such as peracetic acid and m chloroperbenzoic acid (MCPBA), hydrogen peroxide, alkylhyroperoxides such as tert-butyl hydroperoxide. Such methods for the preparation of N-oxides have been described and reviewed in the literature, as for example: T. L. Gilchrist in *Comprehensive Organic Synthesis*, vol. 7, pp 748–750 and in *Advances in Heterocyclic Chemistry*, vol. 9, pp 285–291, vol. 22, pp 390–392 and vol. 43, pp 149–161, A. R. Katritzky. Ed., Academic Press.

Compounds of the invention include compounds of formula I, isotopes thereof, geometric and stereoisomers thereof, N-oxides thereof, and agriculturally suitable salts thereof. The compounds of the invention can exist as one or more stereoisomers. The various isotopes include compounds of formula I, in which at least one natural occurring isotope such as a hydrogen or $^{12}C$ carbon atom is replaced by another isotope thereof such as deuterium or $^{13}C$. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or selectively prepare said stereoisomers. The compounds of the invention may be present as a mixture of stereoisomers, individual stereoisomers, or as an optically active form.

The salts of the compounds of the invention include acid-addition salts of inorganic and organic acids such as hydrobromic, hydrochloric, nitric, phosphoric, sulfuric, acetic, butyric, fumaric, lactic, maleic, oxalic, propionic salicylic, tartaric, toluene-sulfonic or valeric acids.

Preferred compounds of the invention for reasons of better activity and/or ease of manufacture or handling are:

(a) Compounds of formula I, wherein Z represents an oxygen atom.

(b) Compounds of formula I, wherein $R^3$ represents a phenyl group being optionally substituted by one or more, e.g. 1 to 3 halogen atoms and/or alkyl and/or haloalkyl groups; or wherein $R^3$ represents a $C_{1-6}$ alkyl or $C_{2-6}$ alkenyl group both groups being optionally substituted by one or more halogen atoms and/or $C_{1-4}$ alkoxy groups, or wherein $R^3$ represents a trialkylsilyl group or a hydrogen atom; $R^3$ especially preferred represents phenyl, 4-fluorphenyl, 4-trifluormethyl-phenyl, $C_1$–$C_4$-alkyl, trimethylsilyl, 2-Methyl-2-propen-1-yl, trifluormethyl, pentafluorethyl or hydrogen.

(c) Compounds of formula I, wherein A represents an optionally substituted phenyl, pyridyl, thienyl or pyrazolyl group, in particular wherein A represents a group selected from the formulae (1), (2), (3), and (4):

(1)

(2)

(3)

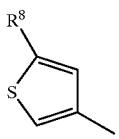

(4)

wherein
R⁸ each independently represents a halogen atom, e.g. chlorine, or an optionally substituted alkyl, alkoxy or thioalkyl group; especially preferred $C_{1-6}$-alkyl or $C_{1-6}$-alkyl substituted by one or more halogene atoms, e.g. chlorine or fluorine, such as trifluormethyl.

R⁹ represents an alkyl group; and n represents an integer of 1 to 5.

(d) Compounds of formula I, wherein m is 0 or 1, Z represents oxygen, A represents a heterocycle of formula (5):

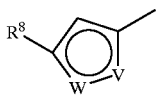

(5)

wherein W—V represents N—CH, S—CH, N—CH—CH, CH—CH—CH or N—NR⁷.

Especially preferred are compounds of formula IA, compound of formula IA

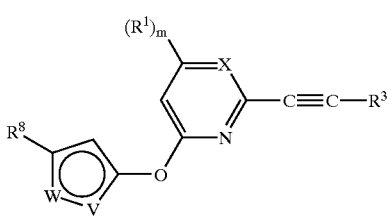

(IA)

wherein X, R¹ and R⁸ are as indicated hereinabove,
R³ represents a formyl group or an alkyl, alkenyl group or an optionally substituted aryl or 5- or 6- membered nitrogen-containing heteroaromatic group, in particular a phenyl group being optionally substituted by one or more halogen atoms and/or alkyl or haloalkyl groups,
W—V represents N—CH, S—CH, N—CH—CH, CH—CH—CH or N—NR⁷; and m is 0 or 1.

Preferably, m is 1 and R¹ represents an $C_{1-6}$ alkyl or $C_{1-6}$ alkoxy group, in particular a methyl, ethyl or methoxy group.

The invention is exemplified by the following specific compounds:

2-(1-methyl-3-trifluoromethylpyrazol-5-yloxy)-4-methyl-6-(2-phenylethynyl)-pyridine; 4-(1-methyl-3-trifluoromethylpyrazol-5-yloxy)-6-methyl-2-(2-phenylethynyl)-pyrimidine; 2-(1-methyl-3-trifluoromethylpyrazol-5-yloxy)-6-(2-phenylethynyl)-pyridine;
4-methoxy-2-(1-methyl-3-trifluoromethylpyrazol-5-yloxy)-6-(2-phenylethynyl)-pyridine; 2-(1-methyl-3-trifluoromethylpyrazol-5-yloxy)-4-methyl-6-(2-trimethylsilylethynyl)-pyridine; 2-(1-methyl-3-trifluoromethylpyrazol-5-yloxy)-4-methyl-6-[2-(4-trifluoromethylphenyl)-ethynyl]-pyridine; 2-(1-methyl-3-trifluoromethylpyrazol-5-yloxy)-4-methyl-6-[2-(4-fluorophenyl)-ethynyl]-pyridine; 6-ethynyl-2-(1-methyl-3-trifluoromethylpyrazol-5-yloxy)-4-methyl-pyridine; 2-(1-methyl-3-trifluoromethylpyrazol-5-yloxy)-4-methyl-6-(4-methylpent-1-yn-3-enyl)-pyridine; 2-(1-methyl-3-trifluoromethylpyrazol-5-yloxy)-4-methyl-6-(3,3-diethoxyprop-1-ynyl)-pyridine; 2-(1-methyl-3-trifluoromethylpyrazol-5-yloxy)-4-methyl-6-(2-formylethynyl)-pyridine; and 2-(1-methyl-3-trifluormethylpyrazol-5-yloxy)-4-methyl-6(4-methyl-pent-1-yn-4-enyl)-pyridine.

The compounds of this invention may be oils, gums, or crystalline solid materials. They can be used in agriculture or related fields for the control of undesired plants. The compounds of general formula I according to the invention possess a high herbicidal activity within a wide concentration range and at low dosages, and may readily be used in agriculture, especially for the selective control of undesired plants such as *Alopecurus myosuroides, Echinochloa crusgalli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application, and particularly in certain crops, such as maize and rice.

The compounds according to the invention can be prepared by conventional methods, particularly as follows:

(A) A suitable process for the preparation of the compounds of formula I comprises the steps of:
a) reacting a respective compound of the general formula II,

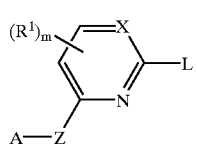

(II)

in which A, R¹, X, Z and m have the same meaning as in formula I, and L represents a suitable leaving group, with a compound of general formula III,

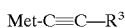

Met-C≡C—R³ (III)

in which R³ has the meaning given, and Met represents a hydrogen or metal atom or an alkylmetal group.

(B) Alternatively, a compound of formula IV:

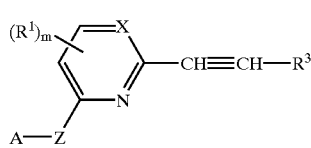

(IV)

in which A, R¹, X, Z and m have the same meaning as in formula I, can be reacted with bromine and subsequently treated with a base.

(C) Alternatively, a compound of formula I, wherein R³ represents an alkenyl group, may be prepared by reacting compound of formula I, wherein R³ represents a formyl group with a Wittig reagent.

The cross coupling reaction (A) generally may be carried out in the presence of a transition metal complex, preferably with Met being a trialkylstannyl or a trialkylsilyl group, as for example described by Rudisill, D. E.; Stille, J. K.; J. Org.Chem.; 54; (1989); 5856–5866, Castro; Stephens; J. Org.Chem.; 28; (1963); 2163; or Stephens; Castro; J. Org.Chem.; 28; (1963); 3313. Preferred transition metals are Pd or Ni. Compounds of general formula II may be prepared and isolated separately or may be prepared in situ.

The reactions according to (A) to (C) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofuran or dioxane, or alcohols, or water, or mixtures thereof. The reactions are carried out at a temperature between ambient temperature and the reflux temperature of the reaction mixture, preferably at elevated temperature, especially at reflux temperature.

The reactions may be carried out in the presence of a base such as an alkali hydroxide, bicarbonate or carbonate, e. g. sodium or potassium hydroxide, bicarbonate or carbonate, an alkali alkoxide, e. g. sodium ethoxide, or an organic base such as triethylamine.

A hydroxy or thio compound used in the above reactions may be present in form of a salt, preferably as a salt of an alkali metal, particularly of sodium or potassium. The presence of a copper salt may be suitable.

Suitable leaving groups L, are each independently e.g. alkylsulfonyl, arylsulfonyl groups, alkylsulfonyloxy, arylsulfonyloxy, perfluoroalkylsulfonyloxy groups, and halogen atoms, in particular methysulfonyl, p-toluenesulfonyl and trifluoromethylsulfonyl groups or fluorine, chlorine and bromine atoms.

For compounds of formula I, II or IV, certain substituents $R^1$ and $R^2$ like alkyl, alkoxy, alkylthio, alkylamino, dialkylamino, amino or halo, can be introduced onto the pyridine or pyrimidine ring by displacement of a alkyl- or arylsulfonyl, alkyl- or arylsulfonyloxy group, or halogen atom, or of a aryl- or hetaryloxy group like A-O group, wherein A has the meaning given. Halogen atoms may also be introduced by diazotization of an amino group. The compounds used as starting material are known or can be prepared analogously to known methods.

Intermediates of formula II can suitably be prepared starting from compounds of formula V,

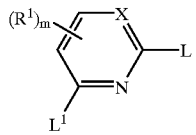

(V)

in which $R^1$, X, L and m have the meaning given above, and $L^1$ has the meaning given for L, by conventional methods known in pyridine chemistry, as described in : G. R. Newkome, "Pyridine and its Derivatives", in The Chemistry of Heterocyclic Compounds, Vol.14, Part 5, Eds. A. Weissberger and E. C. Taylor, John Wiley & Sons, New York—Chichester—Brisbane—Toronto—Singapore 1984.

The present invention also provides the use of the compounds of formula I as herbicides. Further, in accordance with the invention there is provided a method of combating undesired plant growth at a locus by treating the locus with a composition according to the invention or an effective amount of a compound of formula I. As a useful action is by foliar spray application, the locus is most suitably the plants in a crop area, typical crops being cereals, maize, soybean, sunflower or cotton. However, application may also be to the soil for those compounds having pre-emergence herbicidal action, or to the water of paddy rice fields. The dosage of active ingredient used may, for example be in the range of from 0.005 to 3 kg/ha, preferably 0.01 to 1 kg/ha.

The compounds of general formula I have been found to show interesting activity as herbicides. Accordingly, the invention further provides a herbicidal composition comprising a compound of formula I as defined above in association with at least one carrier, and a method of making such a composition which comprises bringing a compound of formula I into association with at least one carrier. Preferably, there are at least two carriers, at least one of which is a surface-active agent.

The invention also provides a method of combating undesired plant growth at a locus, comprising application of such a compound or composition.

Particularly interesting activity has been found against grasses and broad leaf weeds, pre- and post-emergence. Selectivity in important crop species such as wheat, barley, maize, rice and soyabeans has also been found. This activity provides a further aspect of the present invention.

In a method as mentioned above, the dosage of the active ingredient, the compound of general formula I, may, for example, be from 0.005 to 10 kg/ha, suitably 0.01 to 4 kg/ha. The locus may be an agricultural or horticultural locus, comprising, for example, a plant or soil. In a preferred method the locus contains undesired plant growth and treatment is by foliar spray application.

The invention also provides the use of a compound as defined above, as a herbicide. The compounds of general formula I have been found to have herbicidal activity. Accordingly, the invention further provides a herbicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidinone, or γ-butyrolactone, higher alkyl pyrrolidones, e.g. n-octylpyrrolidinone or cyclohexylpyrrolidinone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite.

The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystallization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected as disclosed for example by U.S. Pat. No. 5,705,174.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

Emulsion Concentrate (EC)

| Emulsion Concentrate (EC) | | |
|---|---|---|
| Active Ingredient | Compound of Example 2 | 30% (w/v) |
| Emulsifier(s) | Atlox ® 4856 B/Atlox ® 4858 B [1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A [2] (mixture of $C_9$–$C_{10}$ aromatic hydrocarbons) | to 1000 ml |
| Suspension Concentrate (SC) | | |
| Active Ingredient | Compound of Example 2 | 50% (w/v) |
| Dispersing agent | Soprophor ® FL [3] (polyoxyethylene polyaryl phenyl ether phosphate amine salt) | 3% (w/v) |
| Antifoaming agent | Rhodorsil ® 422 [3] (nonionic aqueous emulsion of polydimethylsiloxanes) | 0.2% (w/v) |
| Structure agent | Kelzan ® S [4] (Xanthan gum) | 0.2% (w/v) |
| Antifreezing agent | Propylene glycol | 5% (w/v) |
| Biocidal agent | Proxel ® [5] (aqueous dipropylene glycol solution containing 20% 1,2-benisothiazo-lin-3-one) | 0.1% (w/v) |
| Water | | to 1000 ml |
| Wettable Powder (WP) | | |
| Active Ingredient | Compound of Example 2 | 60% (w/w) |
| Wetting agent | Atlox ® 4995 [1] (polyoxyethylene alkyl ether) | 2% (w/w) |
| Dispersing | Witcosperse ® D-60 [6] | 3% (w/w) |

-continued

| | | |
|---|---|---|
| agent | (mixture of sodium salts of condensed naphthalene sulfonic acid and alkylarylpolyoxy acetates | |
| Carrier/Filler | Kaolin | 35% (w/w) |

Water Dispersible Granules (WG)

| | | |
|---|---|---|
| Active Ingredient | Compound of Example 2 | 50% (w/w) |
| Dispersing/Binding agent | Witcosperse ® D-450 [6] (mixture of sodium salts of condensed naphthalene sulfonic acid and alkyl sulfonates) | 8% (w/w) |
| Wetting agent | Morwet ® EFW [6] (formaldehyde condensation product) | 2% (w/w) |
| Antifoaming agent | Rhodorsil ® EP 6703 [3] (encapsulated silicone) | 1% (w/w) |
| Disintegrant | Agrimer ® ATF [7] (cross-linked homopolymer of N-vinyl-2-pyrrolidone) | 2% (w/w) |
| Carrier/Filler | Kaolin | 35% (w/w) |

[1] available from ICI Surfactants
[2] available from Deutsche Shell AG
[3] available from Rhône-Poulenc
[4] available from Kelco Co.
[5] available from Zeneca
[6] available from Witco
[7] available from International Speciality Products The compositions of this invention can be applied to the plants or their environment simultaneous with or in succession with other active substances. These other active substances can be either fertilizers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:
ametrydione, metabenzthiazuron, metamitron, metribuzin, 2,4-D, 2,4-DB, 2,4-DP, alachlor, alloxydim, asulam, atrazin, bensulfuron, bentazon, bifenox, bromoxynil, butachlor, chloridazon, chlorimuron, chlorpropham, chlorsulfuron, chlortoluron, cinmethylin, clopyralid, cyanazin, cycloate, cycloxydim, dichlobenil, diclofop, eptame, ethiozin, fenoxaprop, fluazifop, fluometuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, endimethalin, picloram, pretilachlor, propachlor, pyridate, quizalofopethyl, sethoxydim, simetryne, terbutryne, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, thiameturon, thifensulfuron, triasulfuron, oxasulfuron, azimsulfuron, tribenuron, esprocarb, prosulfocarb, terbutylazin, benfuresate, clomazone, di-methazone, dithiopyr, isoxaben, quinchlorac, qinmerac, sulfosate, cyclosulfamuron, imazamox, imazamethapyr, flamprop-M-methyl, flamprop-M-isopropyl, picolinafen, fluthiamid, isoxaflutole, flurtamone, daimuron, bromobutide, methyldimron, dimethenamid, sulcotrione, sulfentrazone, oxadiargyl, acifluorfen, cafenstrole, carfentrazone, diuron, glufosinate.

Mixtures with other active ingredients like fungicides, insecticides, acaricides and nematicides are possible.

A suitable concentrated formulation containing a compound according to the invention can, for example, consist of 100 g of active ingredient (compound of formula I), 30 g of dispersing agent, 3 g of antifoaming agent, 2 g of structure agent, 50 g of anti-freezing agent, 0.5 g of a biocidal agent and water ad 1000 ml. Prior to use, it is diluted with water to give the desired concentration of active ingredient.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

EXAMPLE 1

Preparation of 4-methyl-6-phenylethynyl-2-(1-methyl-3-trifluoromethylpyrazol-5-yloxy)pyridine To a solution of 2-bromo-4-methyl-6-(1-methyl-3-trifluoromethyl-pyrazol-5-yloxy)pyridine (3.0 g, 7.1 mmol), tetrakistriphenyl-phosphine palladium (0.2 g, 1.8 mmol) and 2,6-di-tert-butyl-4-methylphenol (3 crystals) in toluene (40 ml) under a nitrogen atmosphere is added dropwise tributyl-phenylethynyl-stannane (2.9 ml, 7.8 mmol) and the resulting mixture is heated at reflux for 2 hours. After cooling, the reaction mixture is diluted with ethyl acetate, washed with a saturated aqueous solution of sodium bicarbonate and dried. 43% of the product (1.1 g, mp. 56° C.) is obtained by flash chromatography.

EXAMPLE 2

Preparation of 4-methyl-6-(4-fluorophenylethynyl)-2-(1-methyl-3-trifluoromethylpyrazol-5-yloxy)-pyridine To a solution of 4-methyl-6-ethynyl-2-(1-methyl-3-trifluorome-thylpyrazol-5-yloxy)pyridine (1 g, 3.55 mmol) in diisopropylamine (20 ml) under a nitrogen atmosphere are added 4-trifluoromethyl-iodobenzene (1.11 g, 5 mmol), bis-triphenylphosphine palladium dichloride (0.12 g, 0.177 mmol) and copper iodide (0.02, 0.1 mmol) and the mixture is heated at 70 ° C. for 30 min. After cooling, the reaction mixture is diluted with pentane : ethyl acetate 1:1 and the organic phase is washed with water, diluted hydrochloric acid and a saturated aqueous solution of sodium bicarbonate and dried. 81% of the product (1.1 g, mp. 86–87° C.) is obtained by flash chromatography.

EXAMPLE 3

Preparation of 4-methyl-6-formylethynyl-2-(1-methyl-3-trifluoromethylpyrazol-5-yloxy)pyridine A suspension of 4-methyl-6-(3,3-diethoxyprop-1-ynyl)-2-(1-methyl-3-trifluoromethylpyrazol-5-yloxy)pyridine (2.2 g, 5.7 mmol) in trichloromethane (100 ml), water (5 ml) and trichloroacetic acid (3 g) is heated overnight at reflux. After cooling, the reaction mixture is diluted with pentane-:ethyl acetate 1:1 and the organic phase is washed with water and a saturated aqueous solution of sodium bicarbonate and dried. 40% of the product (0.7 g) is obtained by flash chromatography as nearly less crystals of mp 73° C.

EXAMPLE 4

Preparation of 4-methyl-6-(4-methyl-pent-1-yn-3-enyl)-2-(1-methyl-3-trifluoromethylpyrazol-5-yl-oxy)pyridine A mixture of isopropyltriphenylphosphine iodide (0.43 g, 1 mmol) in a dry THF (15 ml) is cooled to −70° C. under an inert gas atmosphere. A 2.5 M solution of butyl lithium (0.44 ml) is added and after stirring at −70° C. for 45 min the mixture is heated at 0° C. for 1 h. Then the mixture is cooled to −70° C. and 4-methyl-6-for-mylethynyl-2-(1-methyl-3-trifluoromethylpyrazol-5-yloxy)pyridine 0.3 g, 1 mmol) is added. After stirring for 30 min at −70° C. the reaction mixture is stirred at ambient temperature for 2 days. The mixture is quenched with water, evaporated and to the water containing residue is added ethyl acetate. The mixture is washed with diluted hydrochloric acid and with water. After drying and evaporation, the product (0.15 g) is obtained by flash chromatogy as nearly colorless crystals of mp 85° C.

EXAMPLES 5 to 197

Further Examples are prepared according to the general method of Example 1 to 4 and are listed in Tables 1 to 5.

TABLE 1

| Example | $R^8$ | $R^{1a}$ | $R^{1b}$ | $R^3$ |
|---|---|---|---|---|
| 5 | $OCF_3$ | $CH_3$ | H | $C_6H_5$ |
| 6 | $SCF_3$ | $CH_3$ | H | $C_6H_5$ |
| 7 | Cl | $CH_3$ | H | $C_6H_5$ |
| 8 | $OCF_3$ | $CH_3$ | H | 4-F—$C_6H_4$ |
| 9 | $SCF_3$ | $CH_3$ | H | 4-F—$C_6H_4$ |
| 10 | Cl | $CH_3$ | H | 4-F—$C_6H_4$ |
| 11 | $CF_3$ | $CH_3$ | H | 4-$CF_3$—$C_6H_4$ |
| 12 | $SCF_3$ | $CH_3$ | H | 4-$CF_3$—$C_6H_4$ |
| 13 | Cl | $CH_3$ | H | 4-$CF_3$—$C_6H_4$ |
| 14 | $CF_3$ | $CH_3$ | H | $Si(CH_3)_3$ |
| 15 | $SCF_3$ | $CH_3$ | H | $Si(CH_3)_3$ |
| 16 | Cl | $CH_3$ | H | $Si(CH_3)_3$ |
| 17 | $OCF_3$ | $CH_3$ | H | H |
| 18 | $SCF_3$ | $CH_3$ | H | H |
| 19 | Cl | $CH_3$ | H | H |
| 20 | $OCF_3$ | $CH_3$ | H | $CH_2$—$C(CH_3)$=$CH_2$ |
| 21 | $SCF_3$ | $CH_3$ | H | $CH_2$—$C(CH_3)$=$CH_2$ |
| 22 | Cl | $CH_3$ | H | $CH_2$—$C(CH_3)$=$CH_2$ |
| 23 | $CF_3$ | H | $OCH_3$ | $C_6H_5$ |
| 24 | $OCF_3$ | H | $OCH_3$ | $C_6H_5$ |
| 25 | $SCF_3$ | H | $OCH_3$ | $C_6H_5$ |
| 26 | Cl | H | $OCH_3$ | $C_6H_5$ |
| 27 | $CF_3$ | $OCH_3$ | H | $C_6H_5$ |
| 28 | $OCF_3$ | $OCH_3$ | H | $C_6H_5$ |

TABLE 1-continued

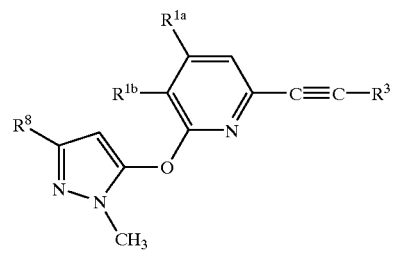

| Example | $R^8$ | $R^{1a}$ | $R^{1b}$ | $R^3$ |
|---|---|---|---|---|
| 29 | $SCF_3$ | $OCH_3$ | H | $C_6H_5$ |
| 30 | Cl | $OCH_3$ | H | $C_6H_5$ |
| 31 | $CF_3$ | H | H | $C_6H_5$ |
| 32 | $CF_3$ | H | H | $C_6H_5$ |
| 33 | $CF_3$ | H | H | $C_6H_5$ |
| 34 | $CF_3$ | H | H | $C_6H_5$ |
| 35 | $CF_3$ | H | $CH_3$ | $CF_3$ |
| 36 | $CF_3$ | H | $CH_3$ | $C_2F_5$ |
| 37 | $CF_3$ | H | $CH_3$ | $CH_3$ |
| 38 | $CF_3$ | H | $CH_3$ | $C_2H_5$ |
| 39 | $CF_3$ | H | $CH_3$ | $C_3H_7$ |
| 40 | $CF_3$ | H | $CH_3$ | $C_4H_9$ |

TABLE 2

| Example | $R^8$ | $R^{1a}$ | $R^{1b}$ | $R^3$ |
|---|---|---|---|---|
| 41 | $OCF_3$ | $CH_3$ | H | $C_6H_5$ |
| 42 | $SCF_3$ | $CH_3$ | H | $C_6H_5$ |
| 43 | Cl | $CH_3$ | H | $C_6H_5$ |
| 44 | $OCF_3$ | $CH_3$ | H | 4-F—$C_6H_4$ |
| 45 | $SCF_3$ | $CH_3$ | H | 4-F—$C_6H_4$ |
| 46 | Cl | $CH_3$ | H | 4-F—$C_6H_4$ |
| 47 | $OCF_3$ | $CH_3$ | H | 4-$CF_3$—$C_6H_4$ |
| 48 | $SCF_3$ | $CH_3$ | H | 4-$CF_3$—$C_6H_4$ |
| 49 | Cl | $CH_3$ | H | 4-$CF_3$—$C_6H_4$ |
| 50 | $OCF_3$ | $CH_3$ | H | $Si(CH_3)_3$ |
| 51 | $SCF_3$ | $CH_3$ | H | $Si(CH_3)_3$ |
| 52 | Cl | $CH_3$ | H | $Si(CH_3)_3$ |
| 53 | $OCH_3$ | $CH_3$ | H | H |
| 54 | $SCF_3$ | $CH_3$ | H | H |
| 55 | Cl | $CH_3$ | H | H |
| 56 | $OCF_3$ | $CH_3$ | H | $CH_2$—$C(CH_3)$=$CH_2$ |
| 57 | $SCF_3$ | $CH_3$ | H | $CH_2$—$C(CH_3)$=$CH_2$ |
| 58 | Cl | $CH_3$ | H | $CH_2$—$C(CH_3)$=$CH_2$ |
| 59 | $CF_3$ | H | $OCH_3$ | $C_6H_5$ |
| 60 | $OCF_3$ | H | $OCH_3$ | $C_6H_5$ |
| 61 | $SCF_3$ | H | $OCH_3$ | $C_6H_5$ |
| 62 | Cl | H | $OCH_3$ | $C_6H_5$ |
| 63 | $CF_3$ | $OCH_3$ | H | $C_6H_5$ |
| 64 | $OCF_3$ | $OCH_3$ | H | $C_6H_5$ |
| 65 | $SCF_3$ | $OCH_3$ | H | $C_6H_5$ |
| 66 | Cl | $OCH_3$ | H | $C_6H_5$ |
| 67 | $CF_3$ | H | H | $C_6H_5$ |
| 68 | $CF_3$ | H | H | $C_6H_5$ |
| 69 | $CF_3$ | H | H | $C_6H_5$ |
| 70 | $CF_3$ | H | H | $C_6H_5$ |
| 71 | $CF_3$ | H | $CH_3$ | $CF_3$ |
| 72 | $CF_3$ | H | $CH_3$ | $C_2F_5$ |

TABLE 2-continued

| Example | R⁸ | R¹ᵃ | R¹ᵇ | R³ |
|---|---|---|---|---|
| 73 | CF₃ | H | CH₃ | CH₃ |
| 74 | CF₃ | H | CH₃ | C₂H₅ |
| 75 | CF₃ | H | CH₃ | C₃H₇ |
| 76 | CF₃ | H | CH₃ | C₄H₉ |
| 77 | CF₃ | H | CH₃ | C₆H₅ |
| 78 | CF₃ | H | CH₃ | 4-F—C₆H₄ |
| 79 | CF₃ | H | CH₃ | 4-CF₃—C₆H₄ |
| 80 | CF₃ | H | CH₃ | CH₂—C(CH₃)=CH₂ |

TABLE 3

| Example | R⁸ | R¹ᵃ | R¹ᵇ | R³ |
|---|---|---|---|---|
| 81 | OCF₃ | CH₃ | H | C₆H₅ |
| 82 | SCF₃ | CH₃ | H | C₆H₅ |
| 83 | Cl | CH₃ | H | C₆H₅ |
| 84 | OCF₃ | CH₃ | H | 4-F—C₆H₄ |
| 85 | SCF₃ | CH₃ | H | 4-F—C₆H₄ |
| 86 | Cl | CH₃ | H | 4-F—C₆H₄ |
| 87 | OCF₃ | CH₃ | H | 4-CF₃—C₆H₄ |
| 88 | SCF₃ | CH₃ | H | 4-CF₃—C₆H₄ |
| 89 | Cl | CH₃ | H | 4-CF₃—C₆H₄ |
| 90 | OCF₃ | CH₃ | H | Si(CH₃)₃ |
| 91 | SCF₃ | CH₃ | H | Si(CH₃)₃ |
| 92 | Cl | CH₃ | H | Si(CH₃)₃ |
| 93 | OCF₃ | CH₃ | H | H |
| 94 | SCF₃ | CH₃ | H | H |
| 95 | Cl | CH₃ | H | H |
| 96 | OCF₃ | CH₃ | H | CH₂—C(CH₃)=CH₂ |
| 97 | SCF₃ | CH₃ | H | CH₂—C(CH₃)=CH₂ |
| 98 | Cl | CH₃ | H | CH₂—C(CH₃)=CH₂ |
| 99 | CF₃ | H | OCH₃ | C₆H₅ |
| 100 | OCF₃ | H | OCH₃ | C₆H₅ |
| 101 | SCF₃ | H | OCH₃ | C₆H₅ |
| 102 | Cl | H | OCH₃ | C₆H₅ |
| 103 | CF₃ | OCH₃ | H | C₆H₅ |
| 104 | OCF₃ | OCH₃ | H | C₆H₅ |
| 105 | SCF₃ | OCH₃ | H | C₆H₅ |
| 106 | Cl | OCH₃ | H | C₆H₅ |
| 107 | CF₃ | H | H | C₆H₅ |
| 108 | CF₃ | H | H | C₆H₅ |
| 109 | CF₃ | H | H | C₆H₅ |
| 110 | CF₃ | H | H | C₆H₅ |
| 111 | CF₃ | H | CH₃ | CF₃ |
| 112 | CF₃ | H | CH₃ | C₂F₅ |
| 113 | CF₃ | H | CH₃ | CH₃ |
| 114 | CF₃ | H | CH₃ | C₂H₅ |
| 115 | CF₃ | H | CH₃ | C₃H₇ |
| 116 | CF₃ | H | CH₃ | C₄H₉ |

TABLE 3-continued

| Example | R⁸ | R¹ᵃ | R¹ᵇ | R³ |
|---|---|---|---|---|
| 117 | CF₃ | H | CH₃ | C₆H₅ |
| 118 | CF₃ | H | CH₃ | 4-F—C₆H₄ |
| 119 | CF₃ | H | CH₃ | 4-CF₃—C₆H₄ |
| 120 | CF₃ | H | CH₃ | CH₂—C(CH₃)=CH₂ |

TABLE 4

| Example | R⁸ | R¹ᵃ | R¹ᵇ | R³ |
|---|---|---|---|---|
| 121 | OCF₃ | CH₃ | H | C₆H₅ |
| 122 | SCF₃ | CH₃ | H | C₆H₅ |
| 123 | Cl | CH₃ | H | C₆H₅ |
| 124 | OCF₃ | CH₃ | H | 4-F—C₆H₄ |
| 125 | SCF₃ | CH₃ | H | 4-F—C₆H₄ |
| 126 | Cl | CH₃ | H | 4-F—C₆H₄ |
| 127 | OCF₃ | CH₃ | H | 4-CF₃—C₆H₄ |
| 128 | SCF₃ | CH₃ | H | 4-CF₃—C₆H₄ |
| 129 | Cl | CH₃ | H | 4-CF₃—C₆H₄ |
| 130 | OCF₃ | CH₃ | H | Si(CH₃)₃ |
| 131 | SCF₃ | CH₃ | H | Si(CH₃)₃ |
| 132 | Cl | CH₃ | H | Si(CH₃)₃ |
| 133 | OCF₃ | CH₃ | H | H |
| 134 | SCF₃ | CH₃ | H | H |
| 135 | Cl | CH₃ | H | H |
| 136 | OCF₃ | CH₃ | H | CH₂—C(CH₃)=CH₂ |
| 137 | SCF₃ | CH₃ | H | CH₂—C(CH₃)=CH₂ |
| 138 | Cl | CH₃ | H | CH₂—C(CH₃)=CH₂ |
| 139 | CF₃ | H | OCH₃ | C₆H₅ |
| 140 | OCF₃ | H | OCH₃ | C₆H₅ |
| 141 | SCF₃ | H | OCH₃ | C₆H₅ |
| 142 | Cl | H | OCH₃ | C₆H₅ |
| 143 | CF₃ | OCH₃ | H | C₆H₅ |
| 144 | OCF₃ | OCH₃ | H | C₆H₅ |
| 145 | SCF₃ | OCH₃ | H | C₆H₅ |
| 146 | Cl | OCH₃ | H | C₆H₅ |
| 147 | CF₃ | H | H | C₆H₅ |
| 148 | CF₃ | H | H | C₆H₅ |
| 149 | CF₃ | H | H | C₆H₅ |
| 150 | CF₃ | H | H | C₆H₅ |
| 151 | CF₃ | H | CH₃ | CF₃ |
| 152 | CF₃ | H | CH₃ | C₂F₅ |
| 153 | CF₃ | H | CH₃ | CH₃ |
| 154 | CF₃ | H | CH₃ | C₂H₅ |
| 155 | CF₃ | H | CH₃ | C₃H₇ |
| 156 | CF₃ | H | CH₃ | C₄H₉ |
| 157 | CF₃ | H | CH₃ | C₆H₅ |
| 158 | CF₃ | H | CH₃ | 4-F—C₆H₄ |
| 159 | CF₃ | H | CH₃ | 4-CF₃—C₆H₄ |
| 160 | CF₃ | H | CH₃ | CH₂—C(CH₃)=CH₂ |

TABLE 5

Structure: pyrazole-pyrimidine with $R^{1a}$, $R^{1b}$, $R^8$, and $C{\equiv}C{-}R^3$ substituents; pyrazole bears N-CH$_3$.

| Example | $R^8$ | $R^{1a}$ | $R^{1b}$ | $R^3$ |
|---|---|---|---|---|
| 161 | CF$_3$ | CH$_3$ | H | C$_6$H$_5$ |
| 162 | OCF$_3$ | CH$_3$ | H | C$_6$H$_5$ |
| 163 | SCF$_3$ | CH$_3$ | H | C$_6$H$_5$ |
| 164 | Cl | CH$_3$ | H | C$_6$H$_5$ |
| 165 | OCF$_3$ | CH$_3$ | H | 4-F—C$_6$H$_4$ |
| 166 | SCF$_3$ | CH$_3$ | H | 4-F—C$_6$H$_4$ |
| 167 | Cl | CH$_3$ | H | 4-F—C$_6$H$_4$ |
| 168 | OCF$_3$ | CH$_3$ | H | 4-CF$_3$—C$_6$H$_4$ |
| 169 | SCF$_3$ | CH$_3$ | H | 4-CF$_3$—C$_6$H$_4$ |
| 170 | Cl | CH$_3$ | H | 4-CF$_3$—C$_6$H$_4$ |
| 171 | OCF$_3$ | CH$_3$ | H | Si(CH$_3$)$_3$ |
| 172 | SCF$_3$ | CH$_3$ | H | Si(CH$_3$)$_3$ |
| 173 | Cl | CH$_3$ | H | Si(CH$_3$)$_3$ |
| 174 | OCF$_3$ | CH$_3$ | H | H |
| 175 | SCF$_3$ | CH$_3$ | H | H |
| 176 | Cl | CH$_3$ | H | H |
| 177 | OCF$_3$ | CH$_3$ | H | CH$_2$—C(CH$_3$)=CH$_2$ |
| 178 | SCF$_3$ | CH$_3$ | H | CH$_2$—C(CH$_3$)=CH$_2$ |
| 179 | Cl | CH$_3$ | H | CH$_2$—C(CH$_3$)=CH$_2$ |
| 180 | CF$_3$ | H | OCH$_3$ | C$_6$H$_5$ |
| 181 | OCF$_3$ | H | OCH$_3$ | C$_6$H$_5$ |
| 182 | SCF$_3$ | H | OCH$_3$ | C$_6$H$_5$ |
| 183 | Cl | H | OCH$_3$ | C$_6$H$_5$ |
| 184 | CF$_3$ | OCH$_3$ | H | C$_6$H$_5$ |
| 185 | OCF$_3$ | OCH$_3$ | H | C$_6$H$_5$ |
| 186 | SCF$_3$ | OCH$_3$ | H | C$_6$H$_5$ |
| 187 | Cl | OCH$_3$ | H | C$_6$H$_5$ |
| 188 | CF$_3$ | H | H | C$_6$H$_5$ |
| 189 | CF$_3$ | H | H | C$_6$H$_5$ |
| 190 | CF$_3$ | H | H | C$_6$H$_5$ |
| 191 | CF$_3$ | H | H | C$_6$H$_5$ |
| 192 | CF$_3$ | H | CH$_3$ | CF$_3$ |
| 193 | CF$_3$ | H | CH$_3$ | C$_2$F$_5$ |
| 194 | CF$_3$ | H | CH$_3$ | CH$_3$ |
| 195 | CF$_3$ | H | CH$_3$ | C$_2$H$_5$ |
| 196 | CF$_3$ | H | CH$_3$ | C$_3$H$_7$ |
| 197 | CF$_3$ | H | CH$_3$ | C$_4$H$_9$ |

Herbicidal Activity

To evaluate their herbicidal activity, compounds according to the invention are tested using a representative range of plants:

| | | |
|---|---|---|
| ABUTH | Abutilon theophrasti | velvetweed |
| AMBEL | Ambrosia artemisifolia | ragweed |
| CASOB | Cassia obtusifolia | sicklepod |
| GALAP | Galium aparine | bedstraw |
| IPOHE | Ipomoea hederacea | morningglory |
| LAMPU | Lamium purpureum | deadnettle |
| MATIN | Matricaria inodora | maywed |
| STEME | Stellaria media | chickweed |
| ALOMY | Alopecurus myosuroides | blackgrass |
| DIGSA | Digitaria sanguinalis | crabgrass |
| ECHCG | Echinochloa crusgalli | barnyard grass |
| LOLMU | Lolium multiflorum | ryegrass |
| SETVI | Setaria viridis | foxtail |
| GLXMA | Glycine max | soybean |
| ORYSA | Orysa sativa | rice |
| TRZAW | Triticum aestivum | wheat |
| ZEAMX | Zea mays | corn |

1. Pre-Emergence Test

The pre-emergence tests involve spraying a liquid formulation of the compound onto the soil in which the seeds of the plant species mentioned above has recently been sown.

The soil used in the tests is a prepared horticultural loam. The formulations used in the tests are prepared from solutions of the test compounds in acetone containing 0.4% by weight of an alkyl-phenol/ethylene oxide condensate available under the trade mark TRITON X-155. These acetone solutions are diluted with water and the resulting formulations applied at dosage levels corresponding to 0.013 kg, 0.025 kg, 0.100 kg or 0.400 kg of active material per hectare in a volume equivalent to 900 litres per hectare. In these tests untreated sown soil are used as controls. From 2 to 4 weeks after treatment, the tests are terminated and each pot is examined and rated according to the rating system set forth below:

| Rating System | % Difference in Growth Versus Untreated Control |
|---|---|
| 0-No effect | 0 |
| 1-Trace effect | 1–5 |
| 2-Slight effect | 6–15 |
| 3-Moderate effect | 16–29 |
| 4-Injury | 30–44 |
| 5-Definite injury | 45–64 |
| 6-Herbicidal effect | 65–79 |
| 7-Good herbicidal effect | 80–90 |
| 8-Approaching complete kill | 91–99 |
| 9-Complete kill | 100 |

The results of the assessment are set out in Table 6.

TABLE 6

Assessment (pre-emergence application) 3 weeks after treatment

| Example | Rate A [kg/ha] | ABU-TH | AMB-EL | CAS-OB | GAL-AP | IPO-HE | LAM-PU | MAT-IN | STE-ME | ALO-MY | DIG-SA | ECH-CG | SET-VI | GLX-MA | ORY-SA | TRZ-WA | ZEA-MX |
|---|---|---|---|---|---|---|---|---|---|---|---|---|---|---|---|---|---|
| 1 | 0.400 | 9 | — | 8 | 7 | 9 | 8 | 8 | 9 | 8 | 9 | 8 | 9 | 4 | 5 | 3 | 4 |
|  | 0.100 | 5 | — | X | 3 | 4 | 8 | 8 | 9 | 4 | 9 | 5 | 8 | 3 | 3 | 2 | 2 |
|  | 0.025 | X | — | X | 2 | X | X | 7 | 8 | 2 | 5 | 4 | 7 | X | 2 | 0 | 2 |
|  | 0.013 | 4 | — | 1 | 1 | 3 | 7 | 5 | 5 | 1 | 5 | 1 | 4 | X | 1 | 0 | 1 |
| 2 | 0.400 | 3 | 9 | 7 | — | 6 | — | 9 | — | 8 | — | 7 | 9 | 3 | — | 4 | 2 |
|  | 0.100 | 2 | 6 | 3 | — | 2 | — | 9 | — | 5 | — | 6 | 8 | 2 | — | 2 | 1 |
|  | 0.025 | 1 | 2 | 1 | — | 1 | — | 5 | — | 2 | — | 2 | 4 | 1 | — | 0 | 0 |
|  | 0.013 | 0 | 0 | 0 | — | 0 | — | 1 | — | 1 | — | 1 | 3 | 0 | — | 0 | 0 |
| 14 | 0.400 | 0 | 9 | 3 | 1 | 1 | 9 | 8 | 9 | 7 | 9 | 5 | 5 | 2 | 0 | 1 | 1 |
| 27 | 0.400 | 8 | — | 8 | 6 | 6 | 9 | 8 | 9 | 6 | 8 | 7 | 9 | 3 | 1 | 3 | 3 |
|  | 0.100 | 5 | — | X | 2 | 4 | 8 | 8 | 9 | 3 | 6 | 4 | 8 | 2 | 1 | 2 | 2 |
|  | 0.025 | 5 | — | 7 | 1 | 3 | 8 | 8 | 9 | 2 | 6 | 3 | 5 | 2 | 0 | 1 | 1 |
| 31 | 0.400 | 2 | — | 3 | X | 2 | 8 | 7 | 9 | 3 | 8 | 5 | 8 | 1 | 1 | 0 | 2 |
|  | 0.100 | X | — | 3 | 2 | X | 8 | 6 | 8 | 1 | 5 | 2 | 6 | X | 1 | 0 | 2 |
|  | 0.025 | X | — | 1 | 1 | X | 7 | 2 | 2 | 0 | 2 | 0 | 2 | X | 0 | 0 | 1 |
| 161 | 0.400 | 4 | X | 0 | 3 | 3 | 7 | 8 | X | 3 | 9 | 3 | 7 | 1 | 1 | 0 | 0 |
|  | 0.100 | 4 | 2 | 0 | 1 | 3 | 5 | 4 | X | 1 | 3 | 1 | 4 | 0 | 1 | 0 | 0 |
|  | 0.025 | 2 | 2 | 0 | 1 | 0 | 0 | 3 | X | 9 | 1 | 0 | 2 | 0 | 0 | 0 | 0 |

X = no value
— = not tested

The post-emergence herbicidal activity of the compounds of the present invention is demonstrated by the following test, wherein a variety of monocotyledonous and dicotyledonous plants are treated with formulations prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels equivalent of about 0.025 to 0.4 kg per hectare of test compound per pot. After spraying the plants are placed on greenhouse benches and are cared for in the usual manner, commensurate with conventional greenhouse practices. From 2 to 4 weeks after treatment, the seedling plants are examined and rated according to the rating system provided above. The results of the test are set out in Table 7 below.

TABLE 7

Post-emergence application 2–4 weeks after treatment

| Example | Rate [kg/ha] | ABU-TH | AMB-EL | CAS-OB | GAL-AP | IPO-HE | MAT-IN | STE-ME | ALO-MY | DIG-SA | ECH-CG | SET-VI | GLX-MA | ORY-SA | TRZ-WA | ZEA-MX |
|---|---|---|---|---|---|---|---|---|---|---|---|---|---|---|---|---|
| 1 | 0.400 | 6 | — | 7 | 6 | 8 | 6 | 7 | 8 | 7 | 8 | 8 | 6 | 4 | 3 | 5 |
|  | 0.100 | 5 | — | 7 | 6 | X | 5 | 6 | 7 | 7 | 7 | 8 | 6 | 3 | 3 | 4 |
|  | 0.025 | 4 | — | 6 | 6 | 6 | 4 | 5 | 4 | 3 | 4 | 7 | 5 | 2 | 2 | 2 |
| 2 | 0.400 | 8 | 7 | — | — | 9 | 8 | — | 5 | — | 8 | 9 | 7 | — | 3 | 2 |
|  | 0.100 | 6 | 5 | — | — | 7 | 5 | — | 3 | — | 4 | 7 | 5 | — | 2 | 2 |
|  | 0.025 | 2 | 2 | — | — | 7 | 2 | — | 2 | — | 3 | 4 | 4 | — | 2 | 1 |
| 14 | 0.200 | 1 | 3 |  | — | 8 | 5 | — | 3 | — | 1 | 3 | 4 | — | 1 | 1 |
| 27 | 0.400 | 6 | — | 7 | 7 | 6 | 7 | 8 | 8 | 6 | 7 | 8 | 6 | 3 | 3 | 3 |
|  | 0.100 | 5 | — | 7 | 6 | 6 | 5 | 6 | 6 | 4 | 5 | 7 | 4 | 3 | 2 | 3 |
| 31 | 0.400 | 5 | — | 6 | 6 | 8 | 4 | 6 | 5 | 4 | 5 | 7 | 4 | 2 | 2 | 3 |
|  | 0.100 | 3 | — | 6 | 4 | 7 | 3 | 5 | 3 | 4 | 3 | 5 | 4 | 1 | 1 | 2 |
| 161 | 0.400 | 5 | 5 | 3 | 8 | 9 | 4 | 4 | 3 | 2 | 2 | 6 | X | 3 | 2 | 2 |
|  | 0.100 | 4 | 5 | 1 | 7 | 9 | 3 | 2 | 2 | 2 | 1 | 4 | 3 | 2 | 2 | 2 |

X = no value
— = not tested

What is claimed is:

1. A compound of formula (I)

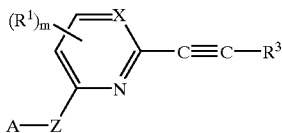

wherein

X represents $CR^2$;

$R^1$ each independently represent a halogen atom or an optionally substituted alkyl, alkenyl, alkinyl, alkoxy, alkoxyalkyl, alkoxyalkoxy group or a haloalkyl, haloalkoxy, cyano, nitro or $SF_5$ group; or $-S(O)_p-R^4$, in which p is 0, 1 or 2, and $R^4$ represents an alkyl or haloalkyl group; or $-NR^5R^6$, in which $R^5$ and $R^6$ each independently represent a hydrogen atom, an alkyl, alkenyl, aralkyl or aryl group, or $R^7O-CY-$, in which $R^7$ represents an alkyl group, and Y represents O or S;

$R^2$ represents a hydrogen atom or has the meaning given for $R^1$;

$R^3$ represents a hydrogen atom or a formyl group or an optionally substituted alkyl, alkenyl, trihydrocarbylsilyl or aryl group, or an optionally substituted 5- or 6-membered nitrogen-containing heteroaromatic group;

A represents an optionally substituted aryl group, an optionally substituted 5- or 6-membered nitrogen-containing heteroaromatic group or an optionally substituted thienyl group;

Z represents an oxygen or sulfur atom; and m is 1 or 2;

or an agronomically acceptable salt or N-oxide thereof.

2. A compound as claimed in claim 1, wherein Z represents an oxygen atom.

3. A compound as claimed in claim 1, wherein $R^3$ represents a phenyl group being optionally substituted by one or more halogen atoms or alkyl or haloalkyl groups.

4. A compound as claimed in claim 1, wherein $R^3$ represents a $C_{1-6}$ alkyl or $C_{2-6}$ alkenyl group being optionally substituted by one or more halogen atoms and/or $C_{1-4}$ alkoxy groups.

5. A compound as claimed in claim 1, wherein A represents an optionally substituted phenyl, pyridyl, thienyl or pyrazolyl group.

6. A compound as claimed in claim 5, wherein A represents a group selected from formulae (1), (2), (3), and (4):

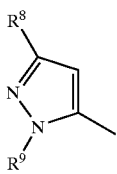

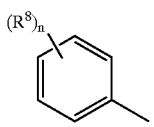

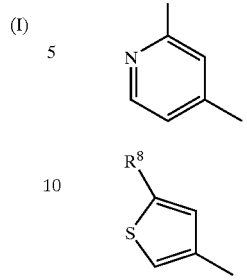

wherein $R^8$ each independently represents a halogen atom or an optionally substituted alkyl, alkenyl, alkoxy or thioalkyl group;

$R^9$ represents an alkyl group; and n represents an integer of 1 to 5.

7. A compound according to claim 1 which is of formula IA

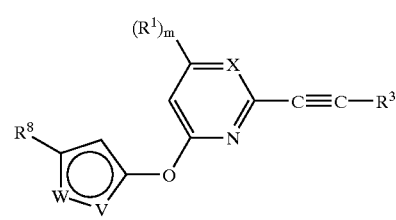

wherein $R^3$ represents a formyl group or an alkyl, alkenyl group or an optionally substituted aryl or 5- or 6-membered nitrogen-containing heteroaromatic group;

W—V represents N—CH, S—CU, N—CH—CH, CH—CH—CH or N—$NR^9$;

m is 1;

$R^8$ represents a halogen atom or an optionally substituted alkyl, alkenyl, alkoxy or thioalkyl group; and $R^9$ represents an alkyl group.

8. A compound of formula (I) according to claim 1 which is selected from the group consisting of 2-(1-methyl-3-trifluoromethyl-pyrazol-5-yloxy)-4-methyl-6-(2-phenylethynyl)-pyridine;

4-methoxy-2-(1-methyl-3-trifluoromethyl-pyrazol-5-yloxy)-6-(2-phenylethynyl)-pyridine;

2-(1-methyl-3-trifluoromethyl-pyrazol 5-yloxy)-4-methyl-6-(2-trimethylsilylethynyl)-pyridine;

2-(1-methyl-3-trifluoromethyl-pyrazol-5-yloxy)-4-methyl-6-[2-(4-trifluoromethyl-phenyl)-ethynyl]-pyridine;

2-(1-methyl-3-trifluoromethyl-pyrazol-5-yloxy)-4-methyl-6-[2-(4-fluoro-phenyl)-ethynyl]-pyridine;

6-ethynyl-2-(1-methyl-3-tritluoromethylpyrazol-5-yloxy)-4-methyl-pyridine;

2-(1-methyl-3-trifluoromethyl-pyrazol-5-yloxy)-4-methyl-6-(4-methylpent-1-yn-3-enyl)-pyridine;

2-(1-methyl-3-trifluoromethyl-pyrazol-5-yloxy)-4-methyl-6-(3,3-diethoxyprop-1-ynyl)-pyridine; and 2-(1-methyl-3-trifluoromethyl-pyrazol-5-yloxy)-4-methyl-6-(2-for-mylethynyl)-pyridine.

9. A compound of formula (I)

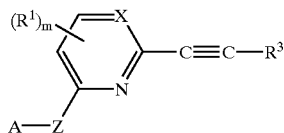

wherein

X represents $CR^2$;

$R^1$ each independently represent a halogen atom or an optionally substituted alkyl, alkenyl, alkinyl, alkoxy, alkoxyalkyl, alkoxyalkoxy group or a haloalkyl, haloalkoxy, cyano, nitro or $SF_5$ group; or $—S(O)_p—R^4$, in which p is 0, 1 or 2, and $R^4$ represents an alkyl or haloalkyl group; or $—NR^5R^6$, in which $R^5$ and $R^6$ each independently represent a hydrogen atom, an alkyl, alkenyl, aralkyl or aryl group, or $R^7O—CY—$, in which $R^7$ represents an alkyl group, and Y represents O or S;

$R^2$ represents a hydrogen atom or has the meaning given for $R^1$;

$R^3$ represents a formyl group or an optionally substituted alkyl, alkenyl, trihydrocarbylsilyl or aryl group, or an optionally substituted 5- or 6-membered nitrogen-containing heteroaromatic group;

A represents an optionally substituted aryl group, an optionally substituted 5- or 6-membered nitrogen-containing heteroaromatic group or an optionally substituted thienyl group;

Z represents an oxygen or sulfur atom; and m is 1 or 2;

or an agronomically acceptable salt or N-oxide thereof.

10. A compound according to claim 9, wherein $R^3$ represents a phenyl group being optionally substituted by one or more halogen atoms or alkyl or haloalkyl groups.

11. A compound according to claim 9, wherein $R^3$ represents a $C_{1-6}$ alkyl or $C_{2-6}$ alkenyl group being optionally substituted by one or more halogen atoms and/or $C_{1-4}$ alkoxy groups.

12. A compound according to claim 9, wherein A represents an optionally substituted phenyl, pyridyl, thienyl or pyrazolyl group.

13. A compound according to claim 12, wherein A represents a group selected from formulae (1), (2), (3), and (4):

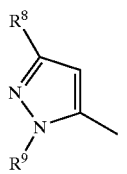

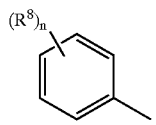

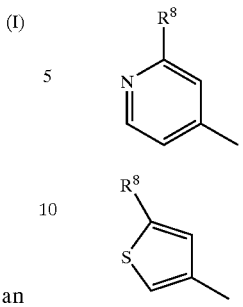

wherein $R^8$ each independently represents a halogen atom or an optionally substituted alkyl, alkenyl, alkoxy or thioalkyl group;

$R^9$ represents an alkyl group; and n represents an integer of 1 to 5.

14. A compound of formula IA

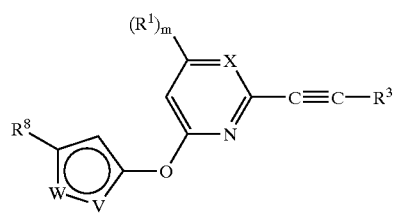

wherein

X represents $CR^2$;

$R^1$ each independently represent a halogen atom or an optionally substituted alkyl, alkenyl, alkinyl, alkoxy, alkoxyalkyl, alkoxyalkoxy group or a haloalkyl, haloalkoxy, cyano, nitro or $SF^5$ group; or $—S(O)_p—R^4$, in which p is 0, 1 or 2, and $R^4$ represents an alkyl or haloalkyl group; or $—NR^5R^6$, in which $R^5$ and $R^6$ each independently represent a hydrogen atom, an alkyl, alkenyl, aralkyl or aryl group, or $R^7O—CY—$, in which $R^7$ represents an alkyl group, and Y represents O or S;

$R^2$ represents a hydrogen atom or has the meaning given for $R^1$;

$R^3$ represents a formyl group or an alkyl, alkenyl group or an optionally substituted aryl or 5- or 6-membered nitrogen-containing heteroaromatic group;

W—V represents N—CH, S—CH, N—CH—CH, CH—CH—CH or N—$NR^9$;

m is 0 or 1;

$R^8$ represents a halogen atom or an optionally substituted alkyl, alkenyl, alkoxy or thioalkyl group; and $R^9$ represents an alkyl group;

or an agronomically acceptable salt or N-oxide thereof.

15. A process for the preparation of the compound of formula I according to claim 1, which comprises reacting a respective compound of formula II,

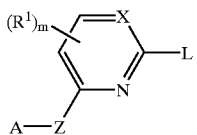

(II)

in which L represents a suitable leaving group, with a compound of formula III,

Met—C≡C—R³    (III)

in which Met represents a hydrogen or metal atom or an alkylmetal group.

16. A herbicidal composition comprising a herbicidally effective amount of at least one compound of formula I according to claim 1 and a carrier.

17. A composition as claimed in claim 16, comprising at least two carriers, at least one of which is surface-active agent.

18. A herbicidal composition according to claim 16, comprising a herbicidally effective amount of at least one compound of formula (I) selected from the group consisting of
- 2-(1-methyl-3-trifluoromethyl-pyrazol-5-yloxy)-4-methyl-6-(2-phenylethynyl)-pyridine;
- 4-methoxy-2-(1-methyl-3-trifluoromethyl-pyrazol-5-yloxy)-6-(2-phenylethynyl)-pyridine;
- 2-(1-methyl-3-trifluoromethyl-pyrazol-5-yloxy)-4-methyl-6-(2-tri-methylsilylethynyl)-pyridine;
- 2-(1-methyl-3-trifluoromethyl-pyrazol-5-yloxy)-4-methyl-6-[2-(4-trifluoromethyl-phenyl)-ethynyl]-pyridine;
- 2-(1-methyl-3-trifluoromethyl-pyrazol-5-yloxy)-4-methyl-6-[2-(4-fluoro-phenyl)-ethynyl]-pyridine;
- 6-ethynyl-2-(1-methyl-3-trifluoromethylpyrazol-5-yloxy)-4-methyl-pyridine;
- 2-(1-methyl-3-trifluoromethyl-pyrazol-5-yloxy)-4-methyl-6-(4-methylpent-1-yn-3-enyl)-pyridine;
- 2-(1-methyl-3-trifluoromethyl-pyrazol-5-yloxy)-4-methyl-6-(3,3-diethoxyprop-1-ynyl)-pyridine; and
- 2-(1-methyl-3-trifluoromethyl-pyrazol-5-yloxy)-4-methyl-6-(2-for-mylethynyl)-pyridine.

19. A method of combating undesired plant growth at a locus, comprising application to the locus of a herbicidally effective amount of at least one compound of formula (I)

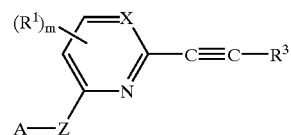

(I)

wherein
X represents CR²;
R¹ each independently represent a halogen atom or an optionally substituted alkyl, alkenyl, alkinyl, alkoxy, alkoxyalkyl, alkoxyalkoxy group or a haloalkyl, haloalkoxy, cyano, nitro or SF⁵ group; or —S(O)ₚ—R⁴, in which p is 0, 1 or 2, and R⁴ represents an alkyl or haloalkyl group; or —NR⁵R⁶, in which R⁵ and R⁶ each independently represent a hydrogen atom, an alkyl, alkenyl, aralkyl or aryl group, or R⁷O—CY—, in which R⁷ represents an alkyl group, and Y represents O or S;
R² represents a hydrogen atom or has the meaning given for R¹;
R³ represents a hydrogen atom or a formyl group or an optionally substituted alkyl, alkenyl, trihydrocarbylsilyl or aryl group, or an optionally substituted 5- or 6-membered nitrogen-containing heteroaromatic group;
A represents an optionally substituted aryl group, an optionally substituted 5- or 6-membered nitrogen-containing heteroaromatic group or an optionally substituted thienyl group;
Z represents an oxygen or sulfur atom; and
m is 0, 1 or 2;
or an agronomically acceptable salt or N-oxide thereof.

20. A method of combating undesired plant growth at a locus, which comprises applying to the locus a herbicidally effective amount of at least one compound of formula (I) as defined in claim 1 or an agronomically acceptable salt or N-oxide thereof.

* * * * *

UNITED STATES PATENT AND TRADEMARK OFFICE
CERTIFICATE OF CORRECTION

PATENT NO. : 6,872,690 B2 Page 1 of 1
APPLICATION NO. : 10/087066
DATED : March 29, 2005
INVENTOR(S) : Maier It is certified that error appears in the above-identified patent and that said Letters Patent is hereby corrected as shown below:

Column 22,
Line 39, delete "W-V represents N-CH, S-CU, N-CH-CH," and substitute
-- W-V represents N-CH, S-CH, N-CH-CH, --.
Line 52, delete "2-(1-methyl-3-triflouromethyl-pyrazol 5-yloxy)-4-" and substitute
-- 2-(1-methyl-3-triflouromethyl-pyrazol-5-yloxy)-4- --.
Line 59, delete "6-ethynyl-2-(1-methyl-3-tritlouromethylpyrazol-5-" and substitute
-- 6-ethynyl-2-(1-methyl-3-triflouromethylpyrazol-5- --.
Line 67, delete "methyl-6-(2-for-mylethynyl)-pyridine." and substitute -- methyl-6-(2-formylethynyl)-pyridine. --.

Column 24,
Line 43, delete "haloalkoxy, cyano, nitro or $SF^5$ group; or $-S(O)_p-R^4$" and substitute
-- haloalkoxy, cyano, nitro or $SF_5$ group; or $-S(O)_p-R^4$, --.

Column 25,
Line 45, delete "methyl-6-(2-for-mylethynyl)-pyridine." and substitute
-- methyl-6-(2-formylethynyl)-pyridine. --.

Column 26,
Line 18, delete "haloalkoxy, cyano, nitro or $SF^5$ group; or $-S(O)_p-R^4$" and substitute
-- haloalkoxy, cyano, nitro or $SF_5$ group; or $-S(O)_p-R^4$, --.

Signed and Sealed this

Twenty-seventh Day of June, 2006

JON W. DUDAS
*Director of the United States Patent and Trademark Office*